United States Patent
Cohn (10) Patent No.: US 12,125,398 B1
(45) Date of Patent: Oct. 22, 2024

(54) INTEGRATING HEALTH AND FITNESS DATA WITH PSYCHOLINGUISTIC AND CONTEXTUAL DATA FOR PATTERN RECOGNITION

(71) Applicant: PSYApps LLC, Seaford, NY (US)

(72) Inventor: Michael Cohn, Seaford, NY (US)

(73) Assignee: PSYApps LLC, Seaford, NY (US)

( * ) Notice: Subject to any disclaimer, the term of this patent is extended or adjusted under 35 U.S.C. 154(b) by 1000 days.

(21) Appl. No.: 17/004,835

(22) Filed: Aug. 27, 2020

Related U.S. Application Data (63) Continuation of application No. 16/029,812, filed on Jul. 9, 2018, now abandoned, which is a continuation of application No. 15/162,417, filed on May 23, 2016, now abandoned, which is a continuation-in-part of application No. 14/989,758, filed on Jan. 6, 2016, now abandoned.

(60) Provisional application No. 62/100,224, filed on Jan. 6, 2015.

(51) Int. Cl.
*G09B 19/00* (2006.01)
*G09B 5/02* (2006.01)
*G10L 25/63* (2013.01)
*G16H 10/60* (2018.01)
*G16H 70/00* (2018.01)

(52) U.S. Cl.
CPC .............. *G09B 19/00* (2013.01); *G09B 5/02* (2013.01); *G10L 25/63* (2013.01); *G16H 10/60* (2018.01); *G16H 70/00* (2018.01)

(58) Field of Classification Search
None
See application file for complete search history.

(56) References Cited

U.S. PATENT DOCUMENTS

2003/0212546 A1 11/2003 Shaw
2014/0221866 A1 8/2014 Quy
2015/0105608 A1 4/2015 Lipoma et al.

OTHER PUBLICATIONS

Mehrabian et al., "Non-immediacy between communicator and object of communication in a verbal message: Application to the inference of attitude," J. Consulting Psych., 1966, 30:420-5.

(Continued)

*Primary Examiner* — James B Hull
(74) *Attorney, Agent, or Firm* — Fish & Richardson P.C.

(57) ABSTRACT

Methods, systems, and apparatus for obtaining at least one of text data or voice data as input data including multiple communications; obtaining first time data associated with the input data; analyzing the input data using a psycholinguistic model; obtaining user data comprising physiological data; obtaining second time data associated with the user data; correlating a particular trait with the user data based on the time data to determine a correlation between the particular trait and the user data; and providing an actionable output based on the correlation. Analyzing the input data includes determining a frequency of occurrence of one or more predetermined words in each communication of the multiple communications; determining a trait score, based on the determined frequency, for each communication of the multiple communications; and identifying a particular trait based at least on the trait score satisfying a predetermined threshold.

9 Claims, 4 Drawing Sheets

(56) References Cited

OTHER PUBLICATIONS

Weintraub, "Personality profiles of American presidents as revealed in their public statements: The presidential news conferences of Jimmy Carter and Ronald Reagan," Political Psych., Jun. 1986, 7(2):285-95.

Winter et al., "The personalities of Bush and Gorbachev measured at a distance: Procedures, portraits and policy," Political Psych., Jun. 1991, 12(2): 215-45.

INTEGRATING HEALTH AND FITNESS DATA WITH PSYCHOLINGUISTIC AND CONTEXTUAL DATA FOR PATTERN RECOGNITION

CROSS-REFERENCE TO RELATED APPLICATIONS

This application is a continuation of U.S. application Ser. No. 16/029,812, filed Jul. 9, 2018, which is a continuation of U.S. application Ser. No. 15/162,417, filed May 23, 2016, which is a continuation-in-part of U.S. application Ser. No. 14/989,758, filed on Jan. 6, 2016, which claims priority to provisional U.S. Application Ser. No. 62/100,224, filed on Jan. 6, 2015, each of which is incorporated herein by reference in its entirety.

FIELD

The present specification generally relates to integrating health and fitness data with psycholinguistic and contextual data for pattern recognition.

BACKGROUND

Health and fitness tracking devices are typically used to capture data about an individual's physiology and behavior, but they do not provide a mechanism to track an individual's psychological data (including cognitive and emotional traits, states, and processes) or use that data to automatically provide suggestions to improve a user's health or mental health throughout his/her day.

SUMMARY

In general, one aspect of the subject matter described in this specification may be embodied in systems, and methods performed by data processing apparatuses that include the actions of obtaining at least one of text data or voice data as input data comprising multiple communications; obtaining first time data associated with the input data; analyzing the input data using a psycholinguistic model, the analyzing including: determining a frequency of occurrence of one or more predetermined words in each communication of the plurality of communications; determining a trait score, based on the determined frequency, for each communication of the plurality of communications;

and identifying a particular trait based at least on the trait score satisfying a predetermined threshold; obtaining user data comprising physiological data; obtaining second time data associated with the user data; correlating the particular trait with the user data based at least on the first time data and the second time data to determine a correlation between the particular trait and the user data; and providing an actionable output based on the correlation between the particular trait and the user data.

These and other implementations may each optionally include one or more of the following features. For instance, the user data may further include environmental data. Further, for instance, correlating the particular trait with the user data may include applying a weight function based on the environmental data.

According to another aspect of the subject matter described in this specification, correlating the particular trait with the user data includes applying a regression analysis model. Further, a result of the regression analysis model may be stored, at least one of additional input data and additional user data may be obtained, and the particular trait may be identified based on the result of the regression analysis model and the at least one of additional input data and additional user data. In addition, the input data and the user data may be associated with a particular user, and the result of the regression analysis model may be stored in association with data identifying the particular user.

In certain implementations, the actionable output comprises one or more of: an audible notification, a visual notification, a tactile notification, a graphical display, data transmitted to a monitoring system, an electronic message, a configuration change to an interface or operating system, content delivery protocol changes, and changes to operation of a program, device, appliance, service, virtual assistant, or artificial intelligence.

Other implementations of these aspects include corresponding systems, apparatus, and computer programs, configured to perform the actions of the methods, encoded on computer storage devices. In other implementations, the disclosed methods, systems, apparatus, and computer programs may also include functionalities embedded in microchip, software development kit (SDK), application program interface (API), network architecture and protocol, and the like.

The details of one or more implementations are set forth in the accompanying drawings and the description below. Other features and advantages will become apparent from the description, the drawings, and the claims.

BRIEF DESCRIPTION OF THE DRAWINGS

Like reference numbers and designations in the various drawings indicate like elements.

DETAILED DESCRIPTION

Psychological profiling algorithms may be used to analyze speech and text and determine psychological states, personality traits, social communication patterns, or psychological profiles, or a combination thereof. These techniques extract semantic or grammatical relationships between words in order to determine the meaning or stylistic patterns of, for example, a casual personal text for the purpose of psychological profiling, assessing emotion and cognitive state, identifying relationships, and deriving diagnostics and intervention strategies based on indicators inherent in the changes of these states and relationships over time. This automated analysis of psychological state changes, personality traits, and social communication patterns may utilize semantic and situational indicators in language to detect, predict, and anticipate human behavior. Thus, in accordance with certain embodiments, these text analytics describe a set of linguistic, statistical, and machine learning techniques that model and structure the information content of textual sources for business intelligence, exploratory data analysis, research, investigation, pattern recognition, or the like.

Utilizing psycholinguistics, machine learning algorithms, and text-based content mining of communication content data, in accordance with embodiments described herein, psychological or social states, traits, and patterns of the communicators of the communication content data may be identified and predicted. Although the term psycholinguistic is used herein, the same systems and methods are applicable to similar sentiment, tonal, or any other psychological and sociological focused automated text analysis of communication. The communication content data may be synchronized, combined, and analyzed with additional personal data associated with the communicators, such as health data, or environmental data, or the like, or any combination thereof. That combined analysis may provide more accurate and robust emotion or mood and cognitive state recognition and changes over time, personality and behavioral patterns, or the like, to provide personal insight, analytics for one or more communicators, pattern recognition, anticipation and predictive forecasting, event detection and forecasting, automatic trigger of actions across connected devices and networked environments, or automatic device configuration changes, or any combination thereof.

Accordingly, certain embodiments provide devices that may automatically track user psychological characteristics and integrate health and fitness data with psycholinguistic and contextual data for pattern recognition. In some cases, the devices may integrate various streams of data, including the psychological, health and fitness, and contextual data, and use computer learning to analyze the integrated streams of data in order to derive patterns that are specific to users and, in response, provide users with recommendations based on these patterns.

Figure 1:
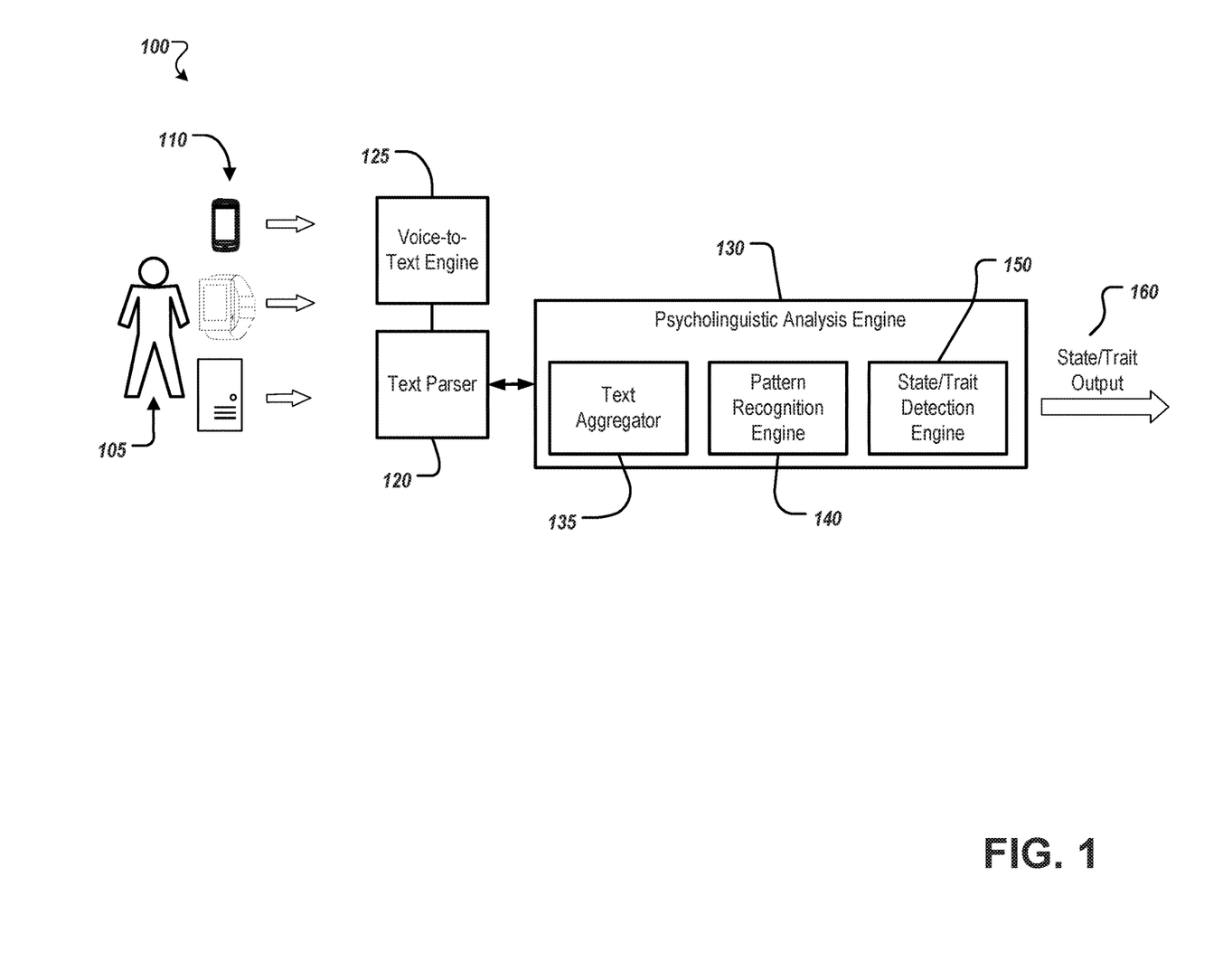
FIG. 1 depicts an example of a system for psycholinguistic analysis of communication content.

FIG. 1 depicts an example of a system 100 for psycholinguistic analysis of communication content. In general, the system 100 receives speech or text of a user 105 and determines a psychological state or trait of the user 105 based on the received speech or text.

In particular, system 100 may include a user 105 as one communicator that produces communication content. In some embodiments, there may be a group of users as communicators. The communication content may be received at or entered into a computing device 110, such as a mobile computing device, laptop, smartphone, cellular phone, tablet, wearable device, digital writing device, server, desktop computer, or the like.

The communication content may include speech, writing, electronic message, images, video, stylus and gesture inputs, or any other additional inputs available for semantic tagging and/or conversion to text for subsequent text analysis, or any combination thereof. Any audio or speech content may be received, for example, at a voice-to-text engine 125. The voice-to-text engine 125 may convert the audio or speech content into text by providing a transcription of the utterances included in the audio or speech content. The text from the voice-to-text engine 125 and text from any writings, electronic messages, images, or the like, or any combination thereof from computing device 110 may be received by text parser 120. The text parser 120 may parse the received text into individual words or phrases. Further, for example, the text parser 120 may separate words, groups of words, or phrases that are relevant to the analysis being performed from words that are not relevant to the analysis. Once parsed, the parsed text may be received by a psycholinguistic analysis engine 130. The psycholinguistic analysis engine 130 may analyze the text to produce a psychological state or trait output 160, examples of which are described below.

Specifically, the psycholinguistic analysis engine 130 may include a text aggregator 135. The text aggregator 135 may categorize the various words and phrases parsed from the text according to the categories used to determine the likely psychological state or trait, and generate or associate with the text other data used to determine the likely state or trait. For example, the text aggregator may categorize words, groups of words, phrases, sentences, or the like, or any combination thereof. Words or phrases may be categorized according to parts of speech, word type, word tense, word length, or the like, or any combination thereof. Words or phrases may additionally or alternatively be categorized into speech categories that relate to measurable psychological state. The text aggregator 135 may generate or associate other data such as the total number of words in a communication, time of day, writing or speech time, number of words per minute, recipient, spelling errors, grammatical errors, words per sentence, and communication rate in terms of at least one of a number of communications per hour or per day, the occurrence of words written in bold face, italics, profanity or email symbols in an alert phrase.

Examples of speech categories or data that may reflect measurable psychological state include quantity of speech, long pauses, rate of speech, nonpersonal references, I, we, me, negatives, qualifiers, retractors, direct references, explainers, expressions of feelings, evaluators, adverbial intensifiers, creative expressions, rhetorical questions, interruptions. Certain psychological profiling algorithms may quantify the number of words in those speech categories. These categories (and algorithms such as the ones described below for determining psychological trait or state based on the categories) are described in more detail in "Verbal Behavior in Everyday Life" by Walter Weintraub (Springer, 1989), which is incorporated herein by reference in its entirety. Other sources of foundational psycholinguistic, sentiment, tonal, or other psychological and sociological focused automated text analysis of communication are provided in the following publications, which are incorporated herein by reference in their entirety: (1) Mehrabian A and Weiner M. Non-immediacy between communicator and object of communication in a verbal message: Application to the inference of attitudes. Journal of Consulting Psychology 1966; 30: 420-425; (2) Weintraub W. Verbal behavior: Adaptation and psychopathology. Springer, 1981; (3) Weintraub W. Personality profiles of American presidents as revealed in their public statements: The presidential news conferences of Jimmy Carter and Ronald Reagan. Political Psychology 1986; 7: 285-295; (4) Winter D G, Hermann, M G, Weintraub W, and Walker S G. The personalities of Bush and Gorbachev measured at a distance: Procedures, portraits and policy. Political Psychology 1991; 2: 215-245.

The psycholinguistic analysis engine 130 may include a pattern recognition engine 140. The pattern recognition engine 140 may apply psychological profiling functions or algorithms to the categorized text and other generated or associated data to develop a score for potential psychological states of the user 105. For example, the algorithms may generally involve determining the number of words in particular categories and developing scores based on the number of words in the categories.

The psychological profiling algorithms may be used to detect various psychological states and may be based, for example, on the following: 1. Indicators of Anger based on increases in the number of: words, personal references, negatives, evaluators, statements of feeling, direct references, rhetorical questions, interruptions, I, and We; and decreases in the number of: qualifiers, and retractors; 2.

Indicators of Anxiety based on increases in the number of: retractors, qualifiers, expressions of feeling, negatives, and explainers; 3. Indicators of Depression based on decreased number of words, increased I, increased me, increased negative key words, increased direct references, increased expressions of feeling key words, increased evaluators, increased adverbial intensifiers; 4. Indicators of Emotional withdrawal based on decreased number of words, decreased number of communications, decreased I score, decreased personal references, decreased expressions of feelings, and decreased evaluators; 5. Indicators of Rigidity or lack of flexibility based on decreased number of qualifiers, decreased number of retractors, decreased we's, increased I's, decreased explainers, increased evaluators, and increased adverbial intensifiers; 6. Indicators of Impulsiveness based on increased retractors and increased expressions of feeling; and 7. Indicators of Emotional instability based on increased I-to-We ratio, increased adverbial intensifiers, increased direct references, increased expression of feelings, increased evaluators. While several measures for communication metrics are described herein, predominantly focused on structural and objective factors in language usage, the described examples are only a non-limiting sample of possible categories. The algorithms and categories may be designed for scanning communication content data for specific words and word phrases, which have demonstrated significant statistical association to various indicators of particular emotional, cognitive, and interpersonal states and traits, detecting and sorting types and intensity. The algorithms may focus on word-usage, but also may learn from the linguistic environment they are operationalized for, adapting through pattern recognition and dynamic weighting.

Without limitation, the psychological profiling algorithms may additionally or alternatively be based on, for example, the following: 1. I scores: high I score—self-preoccupied; moderate I—healthy ability to commit self in thought and action while maintaining degree of autonomy; low I—avoidance of candor, intimacy, commitment; 2. We scores: moderate score-healthy capacity to recognize and collaborate with others; high we+low I—avoidance of intimacy and commitment; 3. Me: high use reflects dependence and passivity; 4. Negatives: high scores associated with stubbornness, opposition, anger, use of denial as defense mechanism; 5. Qualifiers: low score—dogmatism—over-certainty, rigidity; high score—lack of decisiveness, avoidance of commitment; very high score—anxiety; 6. Retractors: high score—difficulty adhering to previous decisions, impulsiveness; moderate—mature capacity to reconsider, flexibility, openness to new possibility; very low—dogmatism, rigidity; 7. Direct References: high scores—difficulty with correspondence or conversation, seeking to distract or manipulate; low or absent—shyness, aloofness, anxiety; 8. Explainers: high—use of rationalization; low or absent—dogmatism, rigidity; 9. Expressions of Feeling: low score—aloofness, hesitant to share feelings, trust; high score—insincere, histrionic; 10. Evaluators: high scores—severe or troubled conscience, psychopathology, anger, dogmatism, rigidity; low scores—fear of intimacy, lack of commitment; 11. Adverbial Intensifiers: high scores indicate histrionic personality, exaggeration, rigidity, judgmental; 12. Rhetorical Questions—increase anger and an effort to control the dialogue; 13. Interruptions—increased anger and an effort to dominate. In certain embodiments, the counts of items in the various categories, conditions, states, traits, or the like may be normalized by either the text aggregator 135 before outputting the count data or by the pattern recognition engine 140 upon receiving the count data. In addition to the metrics described that include parts of speech, structural orientation, as well as subjective indicators like positive and negative, category metrics or taxonomies may also include contextual aspects of language. Further, certain embodiments may include the use of control and precedent sample data sets, containing validated or verifiable types of event, state, trait, or behavior that are found to significantly correlate statistically with the use of particular words, phrases, relationships, and other categories and algorithms.

The psycholinguistic analysis engine 130 may include a state/trait detection engine 150. The state/trait detection engine 150 may identify a particular psychological state or trait for the user 105 based on, for example, a score from the engine 130 satisfying a threshold or correlation to a predetermined pattern or condition. The psycholinguistic analysis engine 130 may output state or trait data. For example, the output may include one or more probabilities respectively associated with one or more identified states or traits.

Another measure of psychological state, which may be referred to as psychological distance, may represent an emotional state expressed by the communicator toward a target, individual or group. Because the communicator normally unconsciously selects the semantic structures used to calculate psychological distance, it may serve as an effective measure of covert attitude. For example, when a communicator's covert attitude, as measured by psychological distances, is compared with overt content of a communicator's remarks, e.g., the number of negative, positive or neutral words associated with the name of an individual or group, an effective measure of deception or bluffing may result. In particular, an indicator of deception may be when the overt attitude toward the person or group is positive and the covert attitude is negative. Conversely, an indicator of bluffing may be when the covert attitude towards the group or individual is more positive than the overt attitude.

Psychological distance may be scored in accordance with the following guidelines. First, each reference by the communicator to the target is identified. Second, the word structures around the reference to the target are evaluated for the presence or absence of each of the nine conditions below. Third, for each time one of these nine conditions is present, a single score is received. Fourth, for each communication, an average psychological distance score is constructed by taking the number of references to the target divided by the number of points received in the communication across all references to the target. This score may be between one and nine and the higher score may indicate, for example, the presence of greater hostility or psychological distance. The nine psychological distance conditions include the following: 1. Spatial: the communicator refers to the object of communication using demonstrative pronouns such as "that" or "those", such as "those people need help" instead of "these people need help;" 2. Temporal: the communicator's relationship with the object of communication is either temporally past or future, such as "X has been showing me his house" instead of "X is showing me his house;" 3. Passivity: the relationship between the communicator and the object of communication is imposed on either or both of them, such as "I have to see X" instead of "I want to see X;" 4. Unilaterally: the relationship between communicator and the object of communication is not mutually determined, such as "I am dancing with X" instead of "X and I are dancing;" 5. Possibility: the relationship between the communicator and the object of communication is possible rather than actual, such as "I could see X" instead of "I want to see X;" 6. Part (of Communicator): only a part, aspect, or characteristic of the communicator is involved in the relationship with the object of communication, such as "My thoughts are about X" instead of "I am thinking of X;" 7. Object (Part of Object): only a part, aspect, or characteristic of the object of communication is involved in the relationship with the communicator, such as "I am concerned about X's future" instead of "I am concerned about X;" 8. Class (of Communicator): a group of people who include the communicator is related to the object of communication, such as "X came to visit us" instead of "X came to visit me;" 9. Class (of Object): the object of communication is related to as a group of objects, which includes the object of communication, such as "I visited X and his wife" instead of "I visited X." Thus, in certain embodiments, the pattern recognition engine 140 may apply functions or algorithms for scoring and/or pattern recognition based on the psychological distance methodology.

Figure 2:
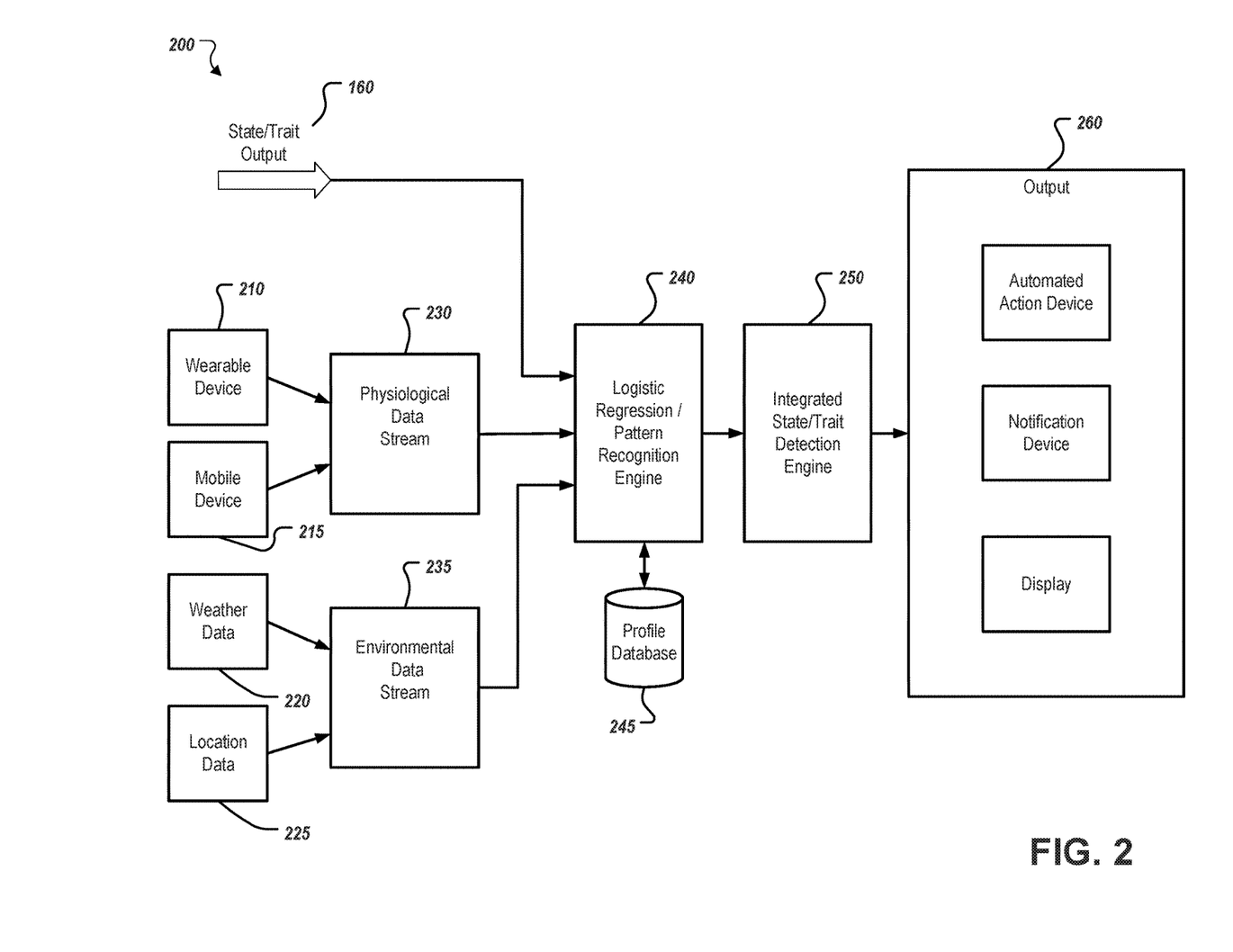
FIG. 2 depicts an example of a system for state and/or trait detection based on pattern recognition of communication content combined with user data.

FIG. 2 depicts an example of a system 200 for state and/or trait detection based on pattern recognition of communication content combined with user data. The system 200 may include a wearable device 210, which may provide physiological data associated with a user of the wearable device 210. The wearable device 210 may include any apparatus, article, item, or other device that may be worn, attached to, embedded in, or coupled with a user, or the like. The system 200 may include a mobile device 215, which may provide physiological data associated with a user of the mobile device 215. The physiological data may be aggregated in a physiological data stream 230. The physiological data may include, for example, health data, exercise data, sleep data, diet data, or the like, or any combination thereof. For example, health data may include heart rate, breathing rate, blood pressure, weight, perspiration, blood glucose level, or the like. Exercise data may include, for example, frequency of exercise, duration of exercise, type of exercise, exercise intensity, calories burned, or the like. Sleep data may include, for example, duration of sleep, time of sleep, quality of sleep, or the like. Diet data may include, for example, type of food and/or drink consumed, number of calories, amount of carbohydrates, amount of fat, amount of sugar, amount of cholesterol, amount of protein, time of meals, or the like.

The system 200 may include one or more sources of weather data 220. The weather data 220 may include past weather data, current weather data, forecasted weather data, or any combination thereof. For example, weather data may include temperature data, barometric pressure data, humidity data, wind data, time and duration of precipitation including rain and snow, time and duration of sun, amount of cloud cover, significant weather events such as tornado, hurricane, flooding, tsunami, or the like. Other environmental data may be included in the weather data 220, such as lunar cycle, solar cycle, tides, or the like. The system 200 may include one or more sources of location data 225. The location data 225 may be based on GPS data or manually entered data. The location data 225 may be associated with the location of the weather data 220. The location data 225 may be associated with the location of the wearable device 210, or mobile device 215, or both. The weather data 220 and the location data 225 may be aggregated in an environmental data stream 235.

Each of the state/trait output 160, the physiological data stream 230, and the environmental data stream 235 may be received at a logistic regression or other pattern recognition engine 240. The logistic regression or pattern recognition engine 240 may perform statistical pattern analysis or modeling such as multivariate co-occurrence to correlate the received data. The logistic regression or pattern recognition engine 240 may access a profile database 245, which may store past input data and user data in association with particular users. The profile database 245 may store, for each respective user, prior recognized patterns or correlations, which may be used to modify the logistic regression or pattern recognition for the currently analyzed data. For example, the state/trait output data 160 and data in the physiological and environmental data streams may be associated with user identifying data, such as a user ID, and the logistic regression or pattern recognition engine 240 may use the user identifying data to access the profile database 245, which may store data in association with user identifying data. The logistic regression or pattern recognition engine 240 may apply functions or algorithms for scoring and/or pattern recognition for particular states, traits, psychological profiles, or the like, or any combination thereof, in combination with the physiological data stream 230. The logistic regression or pattern recognition engine 240 may apply a weighting function based on the environmental data stream 235 for scoring and/or pattern recognition for particular states, traits, psychological profiles, or the like, or any combination thereof. The logistic regression or pattern recognition engine 240 may provide probabilities of respective states or traits based on the analysis of the communication data, the physiological data, and/or the environmental data.

With respect to the pattern recognition engine 240, psychological, social, and behavioral states, traits, conditions, and/or patterns may be influenced, caused, or correlated with any combination of changes and patterns in environmental and physiological conditions and changes. For example, patterns of influence and/or causation may emerge amongst the physiological variables and changes, environmental conditions and their changes, and the psycho-social indicators. Particular physiological and/or environmental variables and changes may preclude or precede certain psychological states, conditions, symptomology and/or behaviors. Additional examples may include the effects of diet, activity, and/or sleep on psychological states, conditions, orientations like depression, productivity, team work, sociability, or the like. Further, for example, environmental conditions, patterns, processes, or changes may influence diet, activity, sleep, or other physiological factors, which then may cause increases in levels of depression, lower productivity, changes in mood, or other psychological states. Pressure changes or light levels, as more subtle exemplary catalysts, may also exert statistically significant trends or changes across the range of psychological, sociological, and behavioral metrics.

Environmental conditions and changes over time may cause, influence, or correlate with physiological data, which then may cause, influence, or correlate with psycho-social-behavioral indicators. In addition, environmental conditions and changes over time may cause, influence, or correlate with both physiological and psycho-social-behavioral indicators simultaneously. For example, patterns and processes in one may precede, cause, influence or correlate with either or both. The confluence need not be linear and the confluence and affect feedback may evolve and reciprocate over time.

The correlation, scoring, recognized pattern, or the like may be received at an integrated state/trait detection engine 250. The integrated state/trait detection engine 250 may identify a particular state or trait based on, for example, a score satisfying a threshold or correlation to a predetermined pattern or condition. For example, the integrated state/trait detection engine 250 may determine that the output from the logistic regression or pattern recognition engine 240 indicates a particular state or trait is likely. For example, the output may include one or more probabilities respectively associated with one or more identified states or traits.

Thus, with the pattern recognition engine 240 and state/trait detection engine 250, strong correlations may be used to anticipate psychological state, trait, condition, or behavior utilizing all or any combination of data to provide one or more of notifications, alerts, recommendations, configuration changes, or the like. Over time, correlations, pattern identification, and reductive analytics calls may also diagnose a likely illness, identify potential problematic symptomology, their causes and catalysts, and in turn aid in more personalized or specialized treatment, intervention strategies, mitigate crisis, and the like. Moreover, data from the environmental data stream 235 may influence the correlations, pattern identifications, or the like, for example, as weighted factors. For example, location data and time-of-year or seasonal data may influence the prioritization or identification of higher potential for certain states or traits.

Based on the indication of a likely state or trait output from the integrated state/trait detection engine 250, an actionable output may be triggered at output device 260. For example, output device 260 may include one or more of an automated action device, a notification device, and a display. At the display, for example, a visual output may be provided in the form of a graph, trend map, data visualization, or other visual indicator. The notification device may provide one or more of a visual notification, an audible notification, and a tactile notification. For example, the visual notification may include one or more of a light, button, message, prompt, or the like. The automated action device may, for example, initiate actions that automatically adjust certain parameters, features, conditions, orders, instructions, or the like, or any combination thereof. For example, automated actions may apply to sorting lists, narrowing or altering search results, recommendations, targeting of content, theme or configuration changes, content delivery, configuration changes to an interface or operating system, or the like, or any combination thereof. These automated actions may be implemented in chat bots, virtual assistants, artificial intelligence devices, connected device networks, appliances, services, and the like.

In accordance with the described algorithms, the output from psycholinguistic analysis may be correlated with one or more of the physiological data stream and the environmental data stream, and patterns may be identified for various input data variables. The actionable outputs may be initiated based on those identified patterns, using either current data or historical data, personalized for a particular user or a group of users, thereby providing a recommendation or prompt, or initiating an action based on the personalized data. As a non-limiting example, a level of depression may be determined to be increasing or exceed a predetermined level based on text analysis in conjunction with a lack of exercise over a predetermined period of time, and/or the weather may be cloudy or rainy. In response to those determinations, a notification may be provided that suggests exercise or parameters for music being played may be adjusted. As another non-limiting example, a level of isolation or anxiety may be determined to be increasing or exceed a predetermined level based on text analysis in conjunction with an increase in heart rate or breathing rate, which may contribute to an indication of anxiety, and may trigger a prompt for a deep breathing exercise. In a further non-limiting example, a level of impulsiveness may be determined to be increasing or exceed a predetermined level based on text analysis in conjunction with a lack of adequate sleep and/or the presence of precipitation. In response to those determinations, a notification may be provided that suggests taking a break from an activity, or a warning against further driving, or recommending sleep. In certain embodiments, the textual analysis may include analyzing interpersonal communication and, in conjunction with physiological data and/or weather data, determining cooperative interaction between people or interpersonal relationship dynamics.

Thus, with the system 100 depicted in FIG. 1 and the system 200 depicted in FIG. 2, psychological data determined based on communication data such as email, electronic message, social media, voice-to-text, handwriting or stylus input, social network data, social graph data, search queries, search history, and/or image or video data may be analyzed in conjunction with behavioral data such as health data, physiological data, sleep data, device use data, and/or other behavioral metrics, as well as environmental data such as location data, weather data, and/or sensor data. The psychological data and behavioral data may be collated, analyzed, and correlated via statistical pattern analysis or multivariate co-occurrence, or the like, and predictive analysis with machine learning for forecasting may be implemented to detect states or traits. The calculated state or trait data may be ranked, sorted, prioritized, or the like, to detect a likely state or trait. Based on the likely state or trait, an actionable output may be provided via threshold triggers, automated actions, notifications, or the like. In addition, an output display may be provided of graphing, trending, visualizations, or the like.

Figure 3:
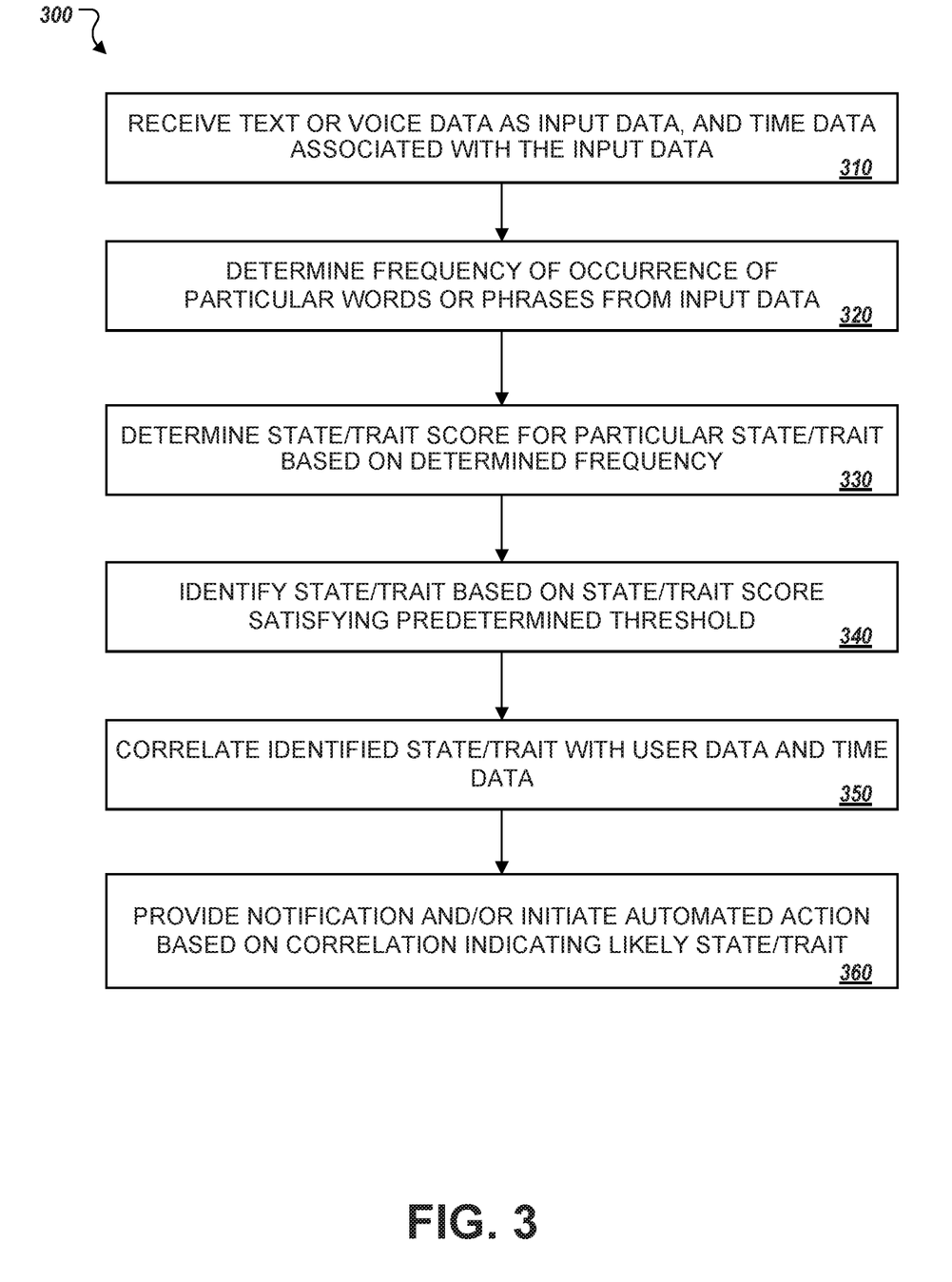
FIG. 3 depicts a flowchart of an example of a process for providing an actionable output based on state and/or trait detection analysis.

FIG. 3 depicts a flowchart of an example of a process 300 for providing an actionable output based on psychological state and/or trait detection analysis. Communication data may be input from computing devices via digital text-based communications, such as SMS (short message service), MMS (multimedia messaging service), email, social network posts, forum posts, blog posts, web content, social network content, social graph data, or any of a variety of other sources of text. Communication data may be input via voice-to-text transcription derived from phone conversation, direct communication with speech recognition enabled device or software, and/or ambient user-specific non-direct non-call-related communication. Any combination of the inputted communication data may be analyzed for psychological, cognitive, emotional, behavioral, content-focused indicators associated with a given focus of interest, application, or the like, as well as time, date, contact frequencies, time patterns, media type, content tags, or the like. Based on that analysis, a formatted and unified coded communication stream or timeline may be derived.

In certain embodiments, a user may be prompted periodically to provide answers to questions or provide certain responses, and those answers or responses may constitute communication data to be analyzed. Psycholinguistic analysis may be performed on the text of the provided answers or responses, and in conjunction with a correlation with physiological data and/or weather data, actionable outputs may be provided.

Additional physiological or behavioral and/or environmental data may be aligned temporally and integrated with the communication data. Physiological data from a wearable device or mobile device, such as activity data, heart rate data, breathing rate data, sleep data, or the like, or any combination thereof may be provided as input data. Device environmental sensor data logs, including GPS, location/time-specific climate and weather conditions, historical weather data and/or solar or lunar cycles may be provided as input data. User device and/or application activity or use logs by application type may be provided as input data. Any combination of the physiological, behavioral or environmental data may be synchronized, formatted, and collated in conjunction with the communication data stream or timeline to derive an integrated and unified communication, physiological, behavioral, environmental data timeline.

Statistical pattern analysis may be performed, such as proprietary and/or open source algorithms, data mining, detection scans or triggers, machine learning, or the like, across the available communication and/or physiological, behavioral, environmental data variables. Based on that analysis, an actionable output may be provided in the form of, for example, personal baseline development across the data integrated analyses for perpetual anomaly detection and machine learning, which may occur across connected apps, devices, platforms, or the like; display screen or holographic-based visualizations; and automatic triggered actions for connected or networked devices such as theme changes, alerts, group or relay notifications. In addition, the system may implement learned personalization for custom content delivery and device adaptation based on pattern recognition, variables or conditions of influence identification and corresponding insight reporting or display, manual or automatic configuration notifications, custom suggestions and/or content delivery. These outputs may vary from real-time to anticipation and prediction.

Referring specifically to FIG. 3, text or voice data may be received as input data at 310. In addition, time data associated with the input data may be received. The text or voice data may include multiple communications associated with one or more communicators. At 320, the input data may be analyzed using a psycholinguistic model by determining a frequency of occurrence of particular words, groups of words, phrases, or sentences in each communication of the multiple communications from the input data. A state or trait score may be determined for a particular state or trait at 330, based on the determined frequency, for each communication of the multiple communications. At 340, a particular state or trait may be identified based at least on the state or trait score satisfying a predetermined threshold. User data including physiological data and time data associated with the user data may be obtained, and the particular state or trait data may be correlated with the user data based at least on the first time data and the second time data to determine a correlation between the particular state or trait and the user data at 350. An actionable output, such as a notification and/or automated action, may be provided at 360 based on the correlation between the particular state or trait and the user data indicating a likely state or trait.

At 350, the obtained user data may include environmental data, and correlating the particular state or trait with the user data may include applying a weight function based on the environmental data. In certain embodiments, correlating the particular trait with the user data at 350 includes applying a regression analysis model. The actionable output at 360 may include one or more of: an audible notification, a visual notification, a tactile notification, a graphical display, data transmitted to a monitoring system, an electronic message, a configuration change to an interface or operating system, content delivery protocol changes, and changes to operation of a program, device, appliance, service, virtual assistant, or artificial intelligence.

The process may further include storing a result of the analysis applied at 350, obtaining at least one of additional input data and additional user data, and identifying the particular state or trait based on the result of the regression analysis model and the at least one of additional input data and additional user data. Further, the input data and the user data may be associated with a particular user, and the result of the analysis applied at 350 may be stored in association with data identifying the particular user.

Some advantages of the systems and processes described herein include integrating health, fitness, physiological, and/or behavioral data, with the insight of psycho-social communication analysis to identify patterns of mood, emotion, cognition, mental clarity, anxiety, uncertainty, decision-making skills, relationship dynamics, or the like, that are expressed in communication with physiological indicators, time, location, environmental data, or the like. The systems and processes described enable an improved analysis of a user's psychological indicators in order to understand how the user's physiological characteristics, activity, sleep, and the weather influence the user's psychological state or trait and to whom and how the user communicates and vice versa. Moreover, the described systems and processes automate several key mood-based indicators that have been dependent on tedious and unreliable manual user input. As users build a baseline of variable input data, the algorithms can provide increasingly valuable individualized insights and predictive outputs. These systems and processes may advantageously provide notifications or suggestions based on weather forecast, amount of sleep, physical activity, or the like, and/or provide alerts about lack of sleep and increased or consistent negativity, such as more rest needed, unclear thinking, indecision, conflict warning, or the like. Thus, for example, the systems and processes described identify patterns of mood, emotion, cognition, mental clarity, anxiety, uncertainty, decision-making skills, relational conflict, and the like expressed in communications based on physiological factors such as activity, sleep, diet, behavior, and environmental factors such as time, location, and weather.

Figure 4:
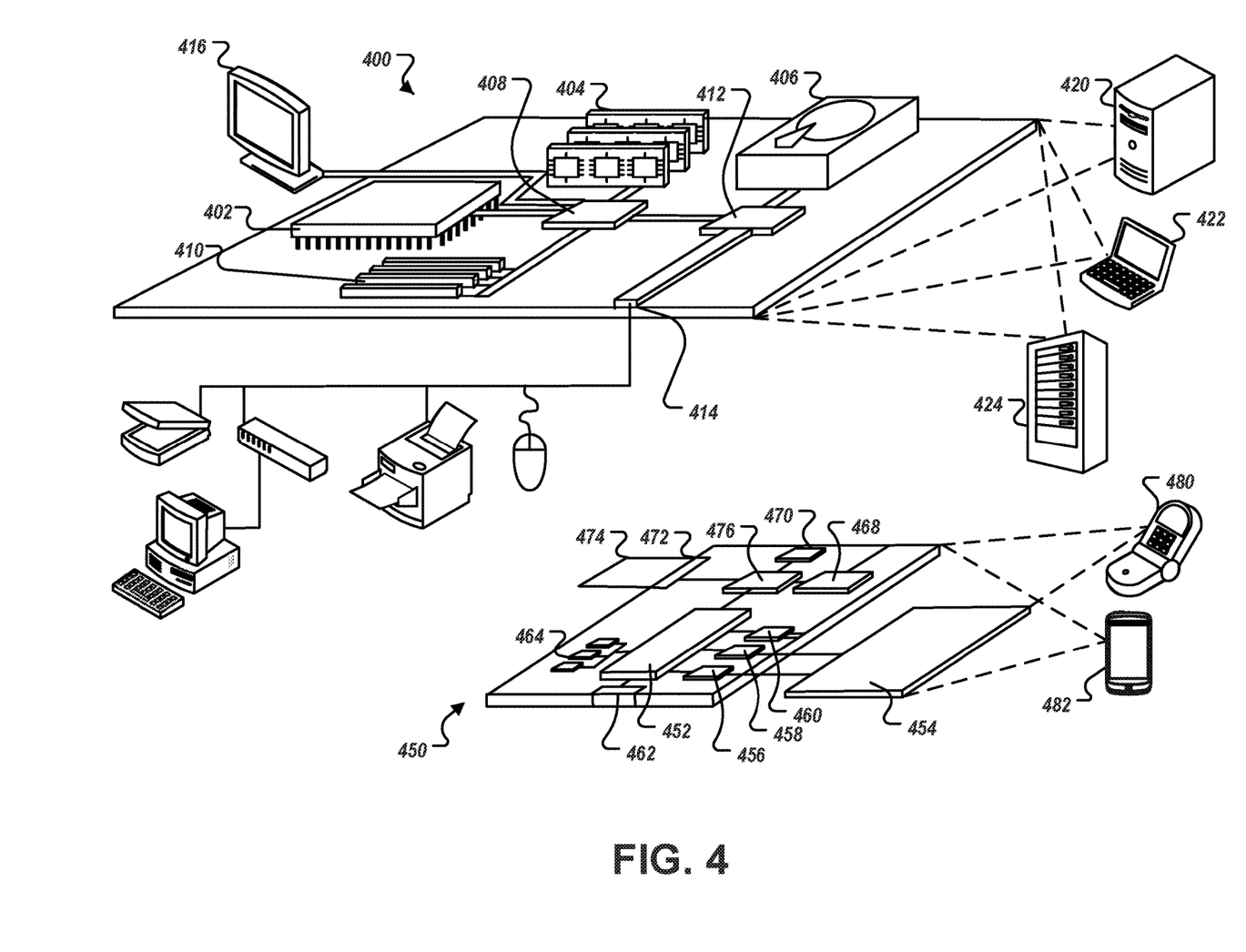
FIG. 4 depicts an example of a computer device and a mobile computer device that may be used to implement the techniques described here.

FIG. 4 depicts an example of a generic computer device 400 and a generic mobile computer device 450, which may be used with the techniques described here. Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be exemplary only, and are not meant to limit implementations described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 may process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 400. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product may be tangibly embodied in an information carrier. The computer program product may also contain instructions that, when executed, perform one or more methods, such as those described above. The information carrier is a computer- or machine-readable medium, such as the memory 404, the storage device 406, or a memory on processor 402.

The high speed controller 408 manages bandwidth-intensive operations for the computing device 400, while the low speed controller 412 manages lower bandwidth-intensive operations. Such allocation of functions is exemplary only. In one implementation, the high-speed controller 408 is coupled to memory 404, display 416 (e.g., through a graphics processor or accelerator), and to high-speed expansion ports 410, which may accept various expansion cards (not shown). In the implementation, low-speed controller 412 is coupled to storage device 406 and low-speed expansion port 414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a microdrive or other device, to provide additional storage. Each of the components 450, 452, 464, 454, 466, and 468, are interconnected using various buses, and several of the components may be mounted on a common motherboard or in other manners as appropriate.

The processor 452 may execute instructions within the computing device 640, including instructions stored in the memory 464. The processor may be implemented as a chipset of chips that include separate and multiple analog and digital processors. The processor may provide, for example, for coordination of the other components of the device 450, such as control of user interfaces, applications run by device 450, and wireless communication by device 450.

Processor 452 may communicate with a user through control interface 648 and display interface 456 coupled to a display 454. The display 454 may be, for example, a TFT LCD (Thin-Film-Transistor Liquid Crystal Display) or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provide in communication with processor 452, so as to enable near area communication of device 450 with other devices. External interface 462 may provide, for example, for wired communication in some implementations, or for wireless communication in other implementations, and multiple interfaces may also be used.

The memory 464 stores information within the computing device 450. The memory 464 may be implemented as one or more of a computer-readable medium or media, a volatile memory unit or units, or a non-volatile memory unit or units. Expansion memory 454 may also be provided and connected to device 450 through expansion interface 452, which may include, for example, a SIMM (Single In Line Memory Module) card interface. Such expansion memory 454 may provide extra storage space for device 450, or may also store applications or other information for device 450. Specifically, expansion memory 454 may include instructions to carry out or supplement the processes described above, and may include secure information also. Thus, for example, expansion memory 454 may be provide as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 454, memory on processor 452, or a propagated signal that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS (Global Positioning System) receiver module 450 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, tablet, or other similar mobile device.

A number of implementations have been described. Nevertheless, it will be understood that various modifications may be made without departing from the spirit and scope of the disclosure. For example, various forms of the flows shown above may be used, with steps re-ordered, added, or removed.

Implementations of the invention and all of the functional operations described in this specification can be implemented in digital electronic circuitry, or in computer software, firmware, or hardware, including the structures disclosed in this specification and their structural equivalents, or in combinations of one or more of them. Implementations of the invention can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These computer programs (also known as programs, software, software applications or code) include machine instructions for a programmable processor, and may be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Functionalities may be embedded in microchip, software development kit (SDK), application program interface (API), network architecture and protocol, and the like. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this disclosure contains many specifics, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Various implementations of the systems and techniques described here may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Thus, particular implementations of the present disclosure have been described. Other implementations are within the scope of the following claims. For example, the actions recited in the claims can be performed in a different order and still achieve desirable results. A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method, comprising:
obtaining, by a server system and from a computing device of a user, data indicating multiple communications provided by the user through the computing device during a particular time period;
parsing, by the server system, the multiple communications to identify (i) a set of terms referenced within the multiple communications, and (ii) a set of linguistic features associated with the set of terms within the multiple communications;
determining, by the server system and based on applying a psycholinguistic model, a set of psycholinguistic states predicted to reflect a present psychological state of the user, wherein the psycholinguistic model is trained to output, for each of sets of different terms, one or more psychological states descriptive of linguistic features associated with a corresponding set of terms;
computing, by the server system and for each psycholinguistic state included in the set of psycholinguistic states, a confidence score based on a respective occurrence frequency of each linguistic feature, from among the set of linguistic features, within the multiple communications, each confidence score representing a probability that a particular psycholinguistic likely corresponds to the present psychological state of the user during the particular time period;
obtaining, by the server system and from the computing device, physiological data of the user collected by one or more sensors associated with the computing device during the particular time period;
training, by the server system, a regression model to output one or more activity patterns based on correlating the multiple communications and the physiological data during the particular time period based on a set of historical activity patterns of the user;
determining, by the server system and based on applying the regression model, that the physiological data includes one or more particular activity patterns that diverge from the set of historical activity patterns of the user;
determining, by the server system, that the physiological data indicates a change to the present psychological state of the user based on determining that the physiological data includes one or more particular activity patterns that diverge from the set of historical activity patterns of the user;
in response to determining that the physiological data indicates a change to the present psychological state of the user, adjusting, by the server system, values of the confidence scores computed for the set of psycholinguistic states;
identifying, by the server system, a subset of psycholinguistic states that have respective adjusted values that satisfy a predetermined threshold value, the subset of psycholinguistic states;
selecting, by the server system, a particular communication from among multiple communications of different types based on the subset of psycholinguistic states; and providing, by the server system, the particular communication for output to the computing device.

2. The method of claim 1, further comprising obtaining environmental data.

3. The method of claim 2, wherein adjusting the values of the confidence scores comprises applying a weight function based on the environmental data.

4. A system comprising:
one or more processors; and
one or more storage devices storing instructions that are operable, when executed by the one or more processors, to cause the one or more processors to perform operations comprising:
obtaining, by a server system and from a computing device of a user, data indicating multiple communications provided by the user through the computing device during a particular time period;
parsing, by the server system, the multiple communications to identify (i) a set of terms referenced within the multiple communications, and (ii) a set of linguistic features associated with the set of terms within the multiple communications;
determining, by the server system and based on applying a psycholinguistic model, a set of psycholinguistic states predicted to reflect a present psychological state of the user, wherein the psycholinguistic model is trained to output, for each of sets of different terms, one or more psychological states descriptive of linguistic features associated with a corresponding set of terms;
computing, by the server system and for each psycholinguistic state included in the set of psycholinguistic states, a confidence score based on a respective occurrence frequency of each linguistic feature, from among the set of linguistic features, within the multiple communications, each confidence score representing a probability that a particular psycholinguistic likely corresponds to the present psychological state of the user during the particular time period;
obtaining, by the server system and from the computing device, physiological data of the user collected by one or more sensors associated with the computing device during the particular time period;
training, by the server system, a regression model to output one or more activity patterns based on correlating the multiple communications and the physiological data during the particular time period based on a set of historical activity patterns of the user;
determining, by the server system and based on applying the regression model, that the physiological data includes one or more particular activity patterns that diverge from the set of historical activity patterns of the user;
determining, by the server system, that the physiological data indicates a change to the present psychological state of the user based on determining that the physiological data includes one or more particular activity patterns that diverge from the set of historical activity patterns of the user;
in response to determining that the physiological data indicates a change to the present psychological state of the user, adjusting, by the server system, values of the confidence scores computed for the set of psycholinguistic states;
identifying, by the server system, a subset of psycholinguistic states that have respective adjusted values that satisfy a predetermined threshold value, the subset of psycholinguistic states;
selecting, by the server system, a particular communication from among multiple communications of different types based on the subset of psycholinguistic states; and
providing, by the server system, the particular communication for output to the computing device.

5. The system of claim 4, further comprising obtaining environmental data.

6. The system of claim 5, wherein adjusting the values of the confidence scores comprises applying a weight function based on the environmental data.

7. A computer-readable storage device storing instructions executable by one or more processors which, upon such execution, cause the one or more processors to perform operations comprising:
obtaining, by a server system and from a computing device of a user, data indicating multiple communications provided by the user through the computing device during a particular time period;
parsing, by the server system, the multiple communications to identify (i) a set of terms referenced within the multiple communications, and (ii) a set of linguistic features associated with the set of terms within the multiple communications;
determining, by the server system and based on applying a psycholinguistic model, a set of psycholinguistic states predicted to reflect a present psychological state of the user, wherein the psycholinguistic model is trained to output, for each of sets of different terms, one or more psychological states descriptive of linguistic features associated with a corresponding set of terms;
computing, by the server system and for each psycholinguistic state included in the set of psycholinguistic states, a confidence score based on a respective occurrence frequency of each linguistic feature, from among the set of linguistic features, within the multiple communications, each confidence score representing a probability that a particular psycholinguistic likely corresponds to the present psychological state of the user during the particular time period;
obtaining, by the server system and from the computing device, physiological data of the user collected by one or more sensors associated with the computing device during the particular time period;
training, by the server system, a regression model to output one or more activity patterns based on correlating the multiple communications and the physiological data during the particular time period based on a set of historical activity patterns of the user;
determining, by the server system and based on applying the regression model, that the physiological data includes one or more particular activity patterns that diverge from the set of historical activity patterns of the user;
determining, by the server system, that the physiological data indicates a change to the present psychological state of the user based on determining that the physiological data includes one or more particular activity patterns that diverge from the set of historical activity patterns of the user;
in response to determining that the physiological data indicates a change to the present psychological state of the user, adjusting, by the server system, values of the confidence scores computed for the set of psycholinguistic states;

identifying, by the server system, a subset of psycholinguistic states that have respective adjusted values that satisfy a predetermined threshold value, the subset of psycholinguistic states;

selecting, by the server system, a particular communication from among multiple communications of different types based on the subset of psycholinguistic states; and providing, by the server system, the particular communication for output to the computing device.

8. The computer-readable storage device of claim 7, further comprising obtaining environmental data.

9. The computer-readable storage device of claim 8, wherein adjusting the values of the confidence scores comprises applying a weight function based on the environmental data.

* * * * *